(12) United States Patent
Sun et al.

(10) Patent No.: US 6,800,634 B2
(45) Date of Patent: Oct. 5, 2004

(54) MODULATORS OF RHO C ACTIVITY

(75) Inventors: Dongxu Sun, Mountain View, CA (US); Edward L. Perkins, Duluth, MN (US); Stuart Tugendreich, Mountain View, CA (US)

(73) Assignee: Iconix Pharmaceuticals Inc., Mountain View, CA (US)

( * ) Notice: Subject to any disclaimer, the term of this patent is extended or adjusted under 35 U.S.C. 154(b) by 0 days.

(21) Appl. No.: 10/300,654

(22) Filed: Nov. 19, 2002

(65) Prior Publication Data

US 2003/0171390 A1 Sep. 11, 2003

Related U.S. Application Data

(60) Provisional application No. 60/331,899, filed on Nov. 19, 2001.

(51) Int. Cl.[7] ..................... A61K 31/473; C07D 221/18
(52) U.S. Cl. ......................................... 514/284; 546/61
(58) Field of Search ............................ 514/284; 546/61

(56) References Cited

FOREIGN PATENT DOCUMENTS

| WO | WO 99/24563 A1 | 5/1999 |
|----|----------------|--------|
| WO | WO 00/32196 A2 | 6/2000 |

OTHER PUBLICATIONS

Aktories, "Rho proteins; targets for bacterial toxins," *Trends Microbiol.* 5(7):282–288, 1997.
Boman et al., "Arf proteins: the membrane traffic police?" *Trends Biochem. Sci.* 20(4):147–150, 1993.
BOS, "ras Oncogenes in human cancer: a review," *Cancer Res.* 49(17):4682–4689, 1989.
Cerione et al., "The Dbl family of oncogenes," *Curr. Ipin. Cell Biol.* 8(2):216–222, 1996.
Chavrier et al., "The role of ARF and Rab GTPases in membrane transport," *Curr. Opin. Cell. Biol.* 11(4):466–475, 1999.
Clark et al., "Genomic analysis of metastasis reveals an essential role for RhoC," *Nature* 406:532–535, 2000.
End, "Farnesyl protein transferase inhibitors and other therapies targeting the Ras signal transduction pathway," *Invest New Drugs* 17(3):241–258, 1999.
Fritz et al., "Rho GTPases are over-expressed in human tumors," *Int. J. Cancer* 81(5):682–687, 1999.
Ganguly et al., "Detection and structural characterization of Ras oncoprotein–inhibitors complexes by electrospray mass spectrometry," *Bioorg. Med. Chem.* 5(5):817–820, 1997.
Ganguly et al., "Interaction of a novel GDP exchange inhibitor with the Ras protein," *Biochemistry* 37(45):15631–15637, 1998.
Hall, "Ras–related proteins," *Curr. Opin. Cell Biol.* 5(2):265–268, 1993.
Hall, "Rho GTPases and the actin cytoskeleton," *Science* 279:509–514, 1998.

Helliwell et al., "The Rho1 effector Pkc1, but not Bni1, mediates signalling from Tor2 to the actin cytoskeleton," *Curr. Biol.* 8(22):1211–1214, 1998.
Ihara et al., "Crystal structure of human RhoA in a dominantly active form complexed with a GTP analogue," *J. Biol. Chem.* 273(16):9656–9666, 1998.
Kaibuchi et al., "Regulation of the cytoskeleton and cell adhesion by the Rho family GTPases in mammalian cells," *Ann. Rev. Biochem.* 68:459–486, 1999.
Kohl, "Farnesyltransferase inhibitors preclinical development," *Ann. NY Acad. Sci.* 886:91–102, 1999.
Kumar et al., "SCH 51344, an inhibitor of Ras/Rac–mediated cell morphology pathway," *Ann. NY Acad. Sci.* 886:122–131, 1999.
Longenecker et al., "How RhoGD1 binds Rho," *Acta Crystallogr. D. Biol. Crystallogr* 55(Pt9):1503–1515, 1999.
Mackay et al., "Rho GTPases," *J. Biol. Chem.* 273:20685–20688, 1998.
Maesaki et al., "The structural basis of Rho effector recognition revealed by the crystal structure of human RhoA complexed with the effector domain of PKN/PRK1," *Mol. Cell* 4(5):793–803, 1999.

(List continued on next page.)

Primary Examiner—Charanjit S. Aulakh
(74) Attorney, Agent, or Firm—Howrey Simon Arnold & White; Adam K. Whiting

(57) ABSTRACT

Compounds of formula 1 modulate the activity of Rho C:

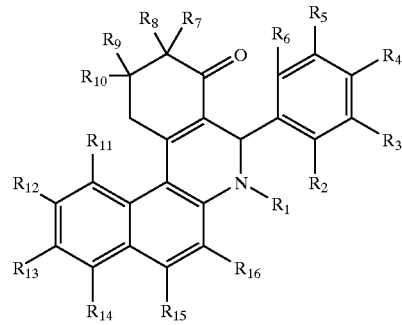

wherein $R_1$ is H, OH, or lower alkyl;

$R_2$, $R_3$, $R_4$, $R_5$, and $R_6$ are each independently H, halo, lower alkyl, OH, lower alkoxy, $NH_2$, lower alkylamino, di(lower alkyl)amino, SH, lower alkylthio, $NO_2$, or two residues together form a heterocyclic ring;

$R_7$, $R_8$, $R_9$, and $R_{10}$ are each independently H, lower alkyl, OH, $NH_2$, aryl, or aralkyl, where aryl and aralkyl are substituted with 0–3 moieties selected from the group consisting of halo, OH, $NH_2$, lower alkyl, lower alkoxy, SH, lower alkylthio, and lower alkylamino;

$R_{11}$, $R_{12}$, $R_{13}$, $R_{14}$, $R_{15}$, and $R_{16}$ are each independently H, halo, lower alkyl, OH, lower alkoxy, or $NO_2$;

or a pharmaceutically acceptable salt thereof.

14 Claims, No Drawings

OTHER PUBLICATIONS

Maesaki et al., "Biochemical and crystallographic characterization of a Rho effector domain of the protein serine/threonine kinase N in a complex with RhoA," *J. Struct. Biol.* 126:166–170, 1999.

Martinez, et al., "Rab proteins," *Biochem Biophys Acta* 1404(1–2):101–112, 1998.

Moore, "Ran and nuclear transport," *J. Biol. Chem.* 273(36):22857–22860, 1998.

Nomanbhoy et al., "Kinetics of cdc42 membrane extraction by Rho–GDI monitored by real–time fluorescence resonance energy transfer," *Biochemistry* 38(6):1744–1750, 1999.

Read et al., "Human RhoA/RhoGDI complex expressed in yeast: GTP exchange is sufficient for translocation of RhoA to liposomes," *Protein Sci.* 9(2):376–386, 2000.

Rittinger et al., "Crystal structure of a small G protein in complex with the GTPase–activating protein rhoGAP," *Nature* 388:693–697, 1997.

Rush et al., "The small nuclear GTPase ran: how much does it run?" *Bioessays* 18(2):103–112, 1996.

Schmidt et al., "Bacterial cytotoxins target Rho GTPases," *Naturwissenschaften* 85(6):253–261, 1998.

Schimmöller et al., "Rab GTPases, directors of vesicle docking," *J. Biol. Chem.* 273(35):22161–22214, 1998.

Shimizu et al., "An open conformation of switch 1 revealed by the crystal structure of a $Mg^{2+}$–free form of RHOA complexed with GDP," *J. Biol. Chem.* 275(24):18311–18317, 2000.

Suwa et al., "Overexpression of the rhoC gene correlates with progression of ductal adenocarcinoma of the pancreas," *Br. J. Cancer* 77(1): 147–152, 1998.

Tanaka et al., "Control of reorganization of the actin cytoskeleton by Rho family small GTP–binding proteins in yeast," *Curr. Opin. Cell Biol.* 10(1):112–116, 1998.

Taveras et al., "Ras oncoprotein inhibitors: the discovery of potent, Ras nucleotide exchange inhibitors and the structural determination of a drug–protein complex," *Bioorg. Med. Chem.* 5(1):125–133, 1997.

Vojtek et al., "Increasing complexity of the Ras signaling pathway," *J. Biol. Chem.* 273(32):19925–19928, 1998.

Watanabe et al., "Cooperation between mDia1 and Rock in Rho–induced actin reorganization," *Nat. Cell Biol.* 1(3):136–143, 1999.

Whitehead et al., "Dbl family proteins," *Biochem. Biophys. Acta* 1332(1):F1–23, 1997.

Yoshioka et al., "Overexpression of small GTP–binding protein RhoA promotes invasion of tumor cells," *Cancer Res.* 59(8):2004–2010, 1999.

Kozlov et al., "Synthesis of new benzo[α]phenanthridine derivatives by condensation of N–arylmethylene–2–naphthylamines with 5–(p–butoxyphenyl)–1,2–cyclohexanedione," *Russian Journal of Organic Chemistry* 36(1):88–92, 2000.

MODULATORS OF RHO C ACTIVITY

CROSS-REFERENCE TO RELATED APPLICATIONS

This application claims the benefit of provisional patent application Ser. No. 60/331,899 filed Nov. 19, 2001, from which application priority is claimed under 35 USC §119 (e)(1) and which application is incorporated herein by reference in its entirety.

FIELD OF THE INVENTION

The claimed invention relates generally to the fields of medicine and enzyme biochemistry. More particularly, the invention relates to compounds and methods for modulating the activity of Rho C.

BACKGROUND OF THE INVENTION

The small GTPase family of proteins are central regulators of cell physiology. Five homologous subfamilies are found in the genomes of all eukaryotes; the S. cerevisiae genome includes 29 proteins in all five families, and the human genome encodes approximately 100 proteins. These five subfamilies have five overlapping but partially distinct functional roles. Ras family members regulate cell growth and division (A. Hall, Curr Opin Cell Biol (1993) 5(2):265–68; A. B. Vojtek et al., J Biol Chem (1998) 273(32):19925–28). Rho family members regulate cell motility, and shape through the actin skeleton (A. Hall, Science (1998) 279:509–14; D. J. Mackay et al., J Biol Chem (1998) 273:20685–88). ARF family members regulate cell adhesion and vesicle trafficking to and from the plasma membrane (A. L. Boman et al., Trends Biochem Sci (1995) 20(4):147–50; P. Chavrier et al., Curr Opin Cell Biol (1999) 11(4):466–75). Rab family members regulate intra-vesicular organelle trafficking (O. Martinez et al., Biochim Biophys Acta (1998) 1404(1–2):101–12; P. Chavrier et al., supra; F. Schimmoller et al., J Biol Chem (1998) 273(35):22161–14) and Ran family members regulate nuclear translocation and chromosomal segregation through regulation of microtubule assembly at the spindle pole (M. S. Moore, J Biol Chem (1998) 273(36):22857–60; M. G. Rush et al., Bioessays (1996) 18(2):103–12). These proteins stimulate other proteins in their GTP-bound state via physical interactions, and lose these associations and activities in the post-hydrolytic GDP-bound state. The hydrolysis reaction thus serves as molecular timer for the events triggered by the GTP-bound small G-protein. In addition, these GTPases also serve as signal integrators since the GTPases are regulated by other signaling pathway proteins; these signaling proteins are themselves regulated and promote or inhibit exchange of GDP for GTP or accelerate the GTP hydrolysis reaction. Ras was the first human small-GTPase to be appreciated in detail due to its identification as a human oncogene mutated in greater than 20% of human cancers (J. L. Bos, Cancer Res (1989) 49(17):4682–89). The ras mutants found in human cancers create a GTPase deficient form of ras which thus exists predominantly in the GTP bound-activated state.

The Rho family of small GTPase comprises more than ten members in humans and six members in yeast. In both organisms, control of the actin skeleton organization and localization is a major Rho function. The human Rho family is composed of three sub-families: Rho, Rac and CDC42 (K. Kaibuchi et al., Ann. Rev. Biochem. (1999) 68:459–86). These sub-families are all involved in control of the actin skeleton and cell adhesion. RhoA is the best-studied of RhoA-G group (collectively Rho) and has been closely associated with actin stress fiber formation in fibroblasts, and through its interaction with ROCK (Rho activated kinase) actin-myosin contraction leading to smooth muscle contraction. Yeast Rho1 is most homologous to human RhoA, and is found at the main site of organized actin in yeast (the bud), where it appears to regulate actin organization associated with budding. In addition, Rho1p controls cell wall bio-synthetic enzyme activity of 1,3-beta-D-glucan synthase (FKS1) during its physical association with the GTP-bound Rho1p. CDC42 and Rac-1 have also been well studied. CDC42 is closely associated with filopodia or microspike formation in fibroblasts and integrin activation. Rac-1 is a downstream component of the Ras signaling pathway from growth factor receptors and is closely associated with actin rearrangements leading to lamellipodia formation in fibroblasts (A. Hall, Science (1998) 279:509–14).

Rho proteins interact with several upstream and downstream components in signaling pathways that originate at the cell membrane with either G-protein coupled receptors, CDC42 and RhoA, or growth factor receptors, such as Rac-1.

The upstream pathways from membrane receptors to the Rho protein involves PI3-Kinase, PIP3, and a Db1-homology protein that is a PIP3 receptor and catalyzes guanine nucleo-tide exchange of Rho; it is thus termed a GEF ("guanine nucleotide exchange factor"). The GEFs for RhoA, and its close homologue RhoC, include Db1, Net1, Ost and Vav. These proteins all have Db1 homology domains (also known as RhoGEF domains) and pleckstrin homology domains, and all activate guanine nucleotide exchange by interaction with Rho proteins through their Db1-homology domain (R. A. Cerione et al., Curr Opin Cell Biol (1996) 8(2):216–22; I. P. Whitehead et al., Biochim Biophys Acta (1997) 1332(1):F1–23). The yeast upstream pathways from the cell membrane to Rho and beyond are highly related to those found in mammalian cells and include Tor2 (yeast PI3-kinase), and Rom1/Rom2 yeast Db1-homology and pleckstrin containing GEFs (K. Tanaka et al., Curr Opin Cell Biol (1998) 10(1):112–16). In both yeast and humans, Rho proteins are prenylated and associate, in their GDP bound states, with a guanine nucleotide-dissociation inhibitor ("GDI"). The GDI, known as RhoGDI in humans, and Rdi1p in yeast, solublizes the Rho protein and prevents its membrane association until activation by a GEF exchanges its GDP for GTP and allows its association with the membrane (T. K. Nomanbhoy et al., Biochemistry (1999) 38(6):1744–50; P. W. Read et al., Protein Sci (2000) 9(2):376–86).

The downstream pathways from Rho family members include many functionally and structurally homologous proteins. RhoA interacts with formin family members Dia1/Dia2, and yeast Rho1p interacts with Bni1 (another formin family member), while CDC42 interacts with WASP and WASP-N, a pair of proteins organized and regulated similarly to formin members. The formin family members have binding sites for the GTP-bound forms of Rho and also actin-nucleating domains whose exposure is controlled by binding of the GTP-Rho (N. Watanabe et al., Nat Cell Biol (1999) 1(3):136–43). In addition to formin interactions, Rho proteins interact with serine/threonine kinases. RhoA interacts with ROCK kinase, which then phosphorylates proteins that control actin polymerization; it also phosphorylates myosin regulators which control contraction in smooth muscles. Yeast Rho1p interacts with PKC1 which launches a MAP kinase cascade leading to control of transcription and the actin skeleton (S. B. Helliwell et al., Curr Biol (1998) 8(22):1211–14; K. Tanaka et al., Curr Opin Cell Biol (1998) 10(1):112–16).

The 3-dimensional structure of RhoA in its GTP, GDP and $Mg^{2+}$ depleted states are known (K. Ihara et al., *J Biol Chem* (1998) 273(16):9656–66; R. Maesaki et al., *Mol Cell* (1999) 4(5):793–803; T. Shimizu et al., *J Biol Chem* (2000) 275 (24):18311–17) as is the structure of RhoA-GTP in complex with an interaction domain of the downstream effector PKN (R. Maesaki et al., supra; R. Maesaki et al., *J Struct Biol* (1999) 126:166–70), and the structure of the complex of RhoA-GDP with Rho-GDI (K. Longenecker et al., *Acta Crystallogr D Biol Crystallogr* (1999) 55(Pt 9): 1503–15). The structure of RhoA in complex with rhoGAP is also known (K. Rittinger et al., *Nature* (1997) 388:693–97). The structure of these molecules combined with similarly detailed data regarding Ras and the Rho family member CDC42 yield consensus molecular mechanism for the GTPase function, GEF's promotion of GDP exchange, GAP's acceleration of GTPase activity and effector stimulation by RhoA-GTP. These studies show the guanine nucleotide bound in a pocket surrounded by three protein loops, known as switch region-I, switch region-II and the P-loop (the phosphate-binding loop). Switch region-I and -II interact extensively with GDI, GEF and effector domains in regions that occlude each other's binding site. Switch region I and II are dramatically rearranged by GTP binding as compared to GDP-bound RhoA and this change exposes large new hydrophobic patches on the switch region surfaces. These newly exposed regions bind effectors.

The importance of Rho proteins in immune cell physiology is highlighted by the evolution of several different mechanisms to inactivate Rho-family proteins by pathogenic Clostridia species and other bacterial pathogens. These toxins are proteins that catalyze several different types of covalent modifications of the switch region-I of Rho proteins. This covalent modifications prevents the correct function of the Rho proteins (K. Aktories, *Trends Microbiol* (1997) 5(7):282–88; G. Schmidt et al., *Naturwissenschaften* (1998) 85(6):253–61). These toxins prevent leukocyte adhesion and diapeadisis and also reduce the production of some anti-bacterial metabolites; thus these toxins confer virulence to the strains possessing them.

Recent reports have shown an important role for Rho in cancer and metastasis. In colon, breast, and lung cancer, RhoA protein expression is elevated compared to the surrounding normal tissue. In breast cancer, RhoA, Rac and CDC42 are elevated. However, RhoA is the most dramatically elevated, and RhoA levels are correlated with disease severity (G. Fritz et al., *Int J Cancer* (1999) 81(5):682–87). In pancreatic cancers, RhoC mRNA levels are elevated in comparison to non-cancerous tissue, and the degree of RhoC elevation is positively correlated with clinical severity and negatively with patient survival. The RhoC elevated phenotype is closely associated with metastasis (H. Suwa et al., *Br J Cancer* (1998) 77(1):147–52). Furthermore, in mice, RhoA transformed-human tumor cells are more invasive than non-transformed cells (K. Yoshioka et al., *Cancer Res* (1999) 59(8):2004–10). Using in-vivo selection for mutations that cause increased metastatic potential in human melanoma cells injected into nude mice, it was recently shown that RhoC overexpression correlates with increased metastatic potential. Over-expression of RhoC from a retroviral vector by itself was sufficient to increase this potential (E. A. Clark et al., *Nature* (2000) 406:532–35). Thus, human cancers express elevated levels of Rho proteins and the degree of elevation correlates with disease severity and poor clinical prognosis.

The compelling case for the involvement of small G-protein in diseases has prompted a number of drug development attempts. Several different geranyl and farnesyl transferase inhibitors have been developed and several are now advanced in the clinic (N. E. Kohl, *Ann NY Acad Sci* (1999) 886:91–102). These inhibitors prevent farnesylation and/or geranylation of many proteins, including the small GTPases, and thus prevent their activity. These inhibitors have shown oral activity in animal models of Ras transformed tumorogenesis. Given their low selectivity and pan-prenylated protein specificity, the low toxicity and apparent high therapeutic ratio these compound have shown is surprising (D. W. End, *Invest New Drugs* (1999) 17(3):241–58; C. C. Kumar et al., *Ann NY Acad Sci* (1999) 886:122–31). An interesting approach to finding wild-type Ras inhibitors used electrospray mass spectrometry to detect compounds that form non-covalent complexes with Ras-GDP. A large library of compounds was screened and several hydroxylamine containing compounds that form complexes with the $Mg^{2+}$ and the exterior lip of switch region-II were found; this binding site was mapped using NMR and a mass-spectrometric footprinting technique. The more avid of these compounds bind with affinities of 0.9 μM (A. K. Ganguly et al., *Bioorg Med Chem* (1997) 5(5):817–20; A. K. Ganguly et al., *Biochemistry* (1998) 37(45):15631–37; A. G. Taveras et al., *Bioorg Med Chem* (1997) 5(1):125–33).

The GTPases present special problems as drug development targets. The difficulties arise due to the functions and properties of these proteins: they exist in numerous, but sometimes transient, complexes with partners (7–10 known partners for each protein). They exist inside most cells as GDP-bound enzymes in a complex with a GDI; their exchange to a GTP bound form happens instantaneously due to the high intracellular concentration of GTP (~1 mM) and their very high affinity for GTP. Their enzymatic activity and turnover is quite slow, and in a practical sense may happen only when a GAP associates with the protein. A specific issue related to discovery of mutant Ras inhibitors is that mutant-Ras forms found in tumors are GTPase deficient, and thus are GTP-bound. The Rho proteins are not locked into a single GTP-bound state, and therefore cycle between states. Thus Rho proteins may be easier targets to inhibit than mutant Ras has proven to be. However, these properties make it especially difficult to assay small G-proteins completely in in-vitro biochemical assays.

SUMMARY OF THE INVENTION

One aspect of the invention is a compound of formula 1

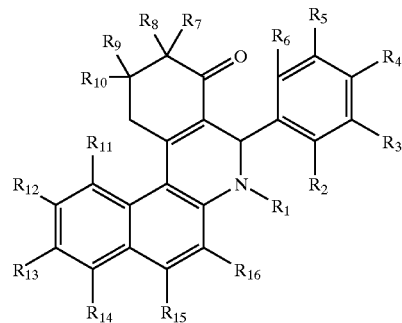

wherein $R_1$ is H, OH, or lower alkyl; $R_2$, $R_3$, $R_4$, $R_5$, and $R_6$ are each independently H, halo, lower alkyl, OH, lower alkoxy, $NH_2$, lower alkylamino, di(lower alkyl) amino, SH, lower alkylthio, $NO_2$, or two residues together form a heterocyclic ring; $R_7$, $R_8$, $R_9$, and $R_{10}$ are each independently H, lower alkyl, OH, $NH_2$, aryl, or aralkyl, where aryl and aralkyl are substituted with 0–3 moieties selected from the group consisting of halo, OH, $NH_2$, lower alkyl, lower alkoxy, SH, lower alkylthio, and lower alkylamino; $R_{11}$, $R_{12}$, $R_{13}$, $R_{14}$, $R_{15}$, and $R_{16}$ are each independently H, halo, lower alkyl, OH, lower alkoxy, or $NO_2$; and pharmaceutically acceptable salts thereof.

Another aspect of the invention is a method for inhibiting Rho C enzyme activity, by contacting said enzyme with a compound of formula 1.

Another aspect of the invention is a formulation for treating a disorder mediated by RhoC, comprising an effective amount of a compound of formula 1, and a pharmaceutically acceptable carrier.

DETAILED DESCRIPTION

Definitions:

Compounds of the invention are compounds of formula 1:

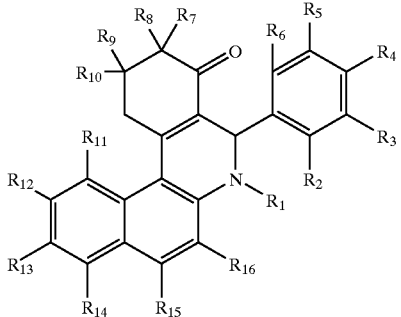

wherein $R_1$ is H, OH, or lower alkyl; $R_2$, $R_3$, $R_4$, $R_5$, and $R_6$ are each independently H, halo, lower alkyl, OH, lower alkoxy, $NH_2$, lower alkylamino, di(lower alkyl)amino, SH, lower alkylthio, $NO_2$, or two residues together form a heterocyclic ring; $R_7$, $R_8$, $R_9$, and $R_{10}$ are each independently H, lower alkyl, OH, $NH_2$, aryl, or aralkyl, where aryl and aralkyl are substituted with 0–3 moieties selected from the group consisting of halo, OH, $NH_2$, lower alkyl, lower alkoxy, SH, lower alkylthio, and lower alkylamino; $R_{11}$, $R_{12}$, $R_{13}$, $R_{14}$, $R_{15}$, and $R_{16}$ are each independently H, halo, lower alkyl, OH, lower alkoxy, or $NO_2$; or a pharmaceutically acceptable salt thereof. Compounds of the invention are named as benzo[a]phenanthridin-4-ones, and are numbered as follows:

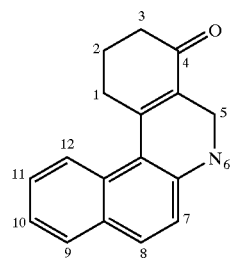

The term "alkyl" as used herein refers to a fully saturated radical consisting only of carbon and hydrogen, having from 1 to about 25 carbon atoms. The term "lower alkyl" refers to an alkyl radical having from 1 to about 6 carbon atoms, such as, for example, methyl, ethyl, propyl, isopropyl, butyl, 3-methylpentyl, hexyl, and the like.

The term "lower alkoxy" refers to a radical of the form RO—, where R is lower alkyl. Suitable examples of lower alkoxy include, without limitation, methoxy, ethoxy, propyloxy, 2-propyloxy, butoxy, t-butoxy, hexyloxy, and the like. Similarly, "lower alkylthio" refers to a radical of the form RS—, where R is lower alkyl. "Lower alkylenedioxy" refers to a diradical of the form —O—R'—O—, where R' is a lower alkyl diradical. Exemplary alkylenedioxy moieties include, without limitation, methylenedioxy, 1,2-ethylenedioxy, 2,2-propylenedioxy, and the like.

The term "aryl" refers to phenyl or naphthyl. "Aralkyl" refers to a moiety of the form Ar—R'—, where Ar is aryl and R' is lower alkylene. Exemplary aralkyl radicals include, without limitation, benzyl, phenethyl, 4-phenylhexyl, 2-naphthylmethyl, 1-naphthylethyl, and the like.

A "heterocyclic ring" as used herein refers to a closed loop of 3–7 atoms containing carbon and at least one atom of O, N, S, and/or P. Heterocyclic rings can be saturated or unsaturated. Exemplary heterocyclic rings include, without limitation, piperidine, furan, tetrahydro-furan, pyrrole, triazole, pyran, tetrahydropyran, thiazole, dioxin, 2,2-dimethyl-1,3-dioxolane, and the like. Heterocyclic rings in the context of this invention will be fused to the phenyl ring that carries $R_2$, $R_3$, $R_4$, $R_5$, and $R_6$, thus forming ring systems such as, for example, benzimidazole, benzofuran, and the like.

The term "halo" as used herein refers to fluoro, chloro, bromo, and iodo.

The term "pharmaceutically acceptable" refers to compounds and derivatives that are not unacceptably toxic to an organism or tissue to be treated.

The term "salt" refers to a derivative of a compound of the invention derived by addition of a simple acid to a basic compound of the invention, or addition of a base to an acidic compound of the invention. For example, compounds of the invention can form acid addition salts, such as hydrochlorides, hydrobromides, acetates, tartarates, citrates, malonates, phosphates, nitrates, sulfates, mesylates, and the like. The term "esters" refers to derivatives of a compound of the invention derived by condensing a compound of the invention having a free —OH group with a carboxylic acid. Exemplary esters include acetates, propionates, citrates, and the like. The term "amides" refers to derivatives of a compound of the invention derived by condensing a compound of the invention having a free —NH group with a carboxylic acid. Exemplary acids include acetic, propionic, citric, malonic, and the like.

The term "modulate" refers to a detectable alteration in an observable enzymatic activity of the target enzyme. The alteration is preferably an inhibition of at least 20%.

The term "effective amount" refers to the quantity of a compound of the invention necessary to inhibit RhoC protein activity, in vitro or in vivo. Such inhibition can be accomplished directly (i.e., by binding directly to RhoC in a way that modulates one or more biological activities) or indirectly (for example, by modifying or interfering with a RhoC ligand that in turn modulates RhoC activity). A "therapeutically effective amount" refers to a quantity of a compound of the invention sufficient to treat a disorder mediated by RhoC activity. Treatment includes preventing or alleviating one or more symptoms of the disorder, preventing the worsening of one or more symptoms, and reducing the likelihood or probability of disease occurring or advancing. Thus, for example, administration of a compound of the invention in order to treat cancer (known or suspected), or to inhibit metastasis of known or suspected tumors, constitutes a treatment within the scope of the invention.

The term "disorder mediated by RhoC" refers to a disease state that is ameliorated by the inhibition of RhoC. Exemplary disorders include, without limitation, cancer and metastasis.

General Method:

One aspect of the invention is a compound of formula 1:

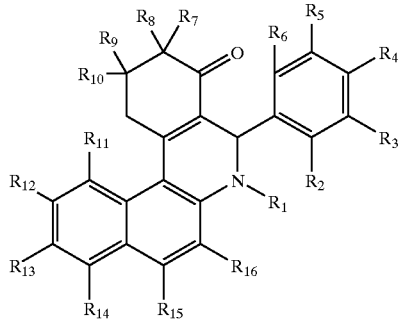

wherein $R_1$ is H, OH, or lower alkyl; $R_2$, $R_3$, $R_4$, $R_5$, and $R_6$ are each independently H, halo, lower alkyl, OH, lower alkoxy, $NH_2$, lower alkylamino, di(lower alkyl)amino, SH, lower alkylthio, $NO_2$, or two residues together form a heterocyclic ring; $R_7$, $R_8$, $R_9$, and $R_{10}$ are each independently H, lower alkyl, OH, $NH_2$, aryl, or aralkyl, where aryl and aralkyl are substituted with 0–3 moieties selected from the group consisting of halo, OH, $NH_2$, lower alkyl, lower alkoxy, SH, lower alkylthio, and lower alkylamino; $R_{11}$, $R_{12}$, $R_{13}$, $R_{14}$, $R_{15}$, and $R_{16}$ are each independently H, halo, lower alkyl, OH, lower alkoxy, or $NO_2$; and pharmaceutically acceptable salts thereof. Preferably at least one of $R_2$, $R_3$, $R_4$, $R_5$, and $R_6$ is not H: more preferably only one or two of $R_2$, $R_3$, $R_4$, $R_5$, and $R_6$ are not H.

Compounds of the invention wherein $R_1$ is H are prepared by condensing an appropriately substituted benzylideneiminyl naphthalene (A) with a substituted 1,3-cyclohexyldione (B) in an inert solvent (for example, a lower alkanol, dimethylsulfoxide, dimethylformamide, N-methylpyrrolidone, 1,3-dimethylimidazolinone, and the like) at about 25 to about 110° C. to provide Compound C. See for example N. G. Kozlov and K. N. Gusak, *Russian J. Org. Chem* (1999) 35:402–14 (1999); N. G. Kozlov, et al., *Russian J. Org. Chem* (2000) 36:88–92 (2000), both incorporated herein by reference in full.

To obtain compounds of the invention wherein $R_1$ is other than H, one can use either of two routes. One method comprises reacting the appropriate N-substituted iminum intermediate (Compound E) with 1,3-diketones B, in an inert solvent (for example, dimethylsulfoxide, dimethylformamide, N-methylpyrrolidone, or 1,3-dimethylimidazolinone), at about 25 to about 110° C., in the presence of a base (for example, a trialkylamine, pyridine, lutidine, collidine, anhydrous potassium carbonate, anhydrous potassium fluoride, or suitable equivalent). An alternate method comprises reacting Compound C with an alkylating agent (for example, an alkyl halide, dialkyl sulfate, alkyl trifluoromethanesulfonate, alkyl methanesulfonate, alkyl arylsulfonate, trialkyl phosphate, trialkyl phosphite or suitable equivalent) in a suitable inert solvent (for example, dimethylsulfoxide, dimethylformamide, N-methylpyrrolidone, or 1,3-di-methylimidazolinone), at about 25 to about 110° C.

Compounds of the invention are assayed for activity using any convenient biochemical or biological assay. For example, one can examine compounds for binding to recombinantly-expressed RhoC, assay compounds for their ability to reverse a RhoC-induced phenotype in a heterologous cell (see e.g., WO99/24563, incorporated herein by reference), or using one or more of the experimental protocols described in the references cited herein. Compounds of the invention demonstrated activity in surrogate genetic assays, in which mammalian RhoA and RhoC proteins were expressed in yeast, producing a screenable phenotype. An effective concentration of test compound specifically reversed the phenotype, demonstrating activity. Compounds were also examined for inhibition of stress fibers, by stimulating NIH 3T3 cells with 10 μM LPA in DMEM+0.2% FBS in the presence of test compounds for 4 hours. Staining with Rhodamine-phalloidin post fixation demonstrated a dose-dependent reduction in the percentage of labeled F-actin, demonstrating inhibition of a RhoC biological activity.

Compounds of the invention can be administered to a subject, or can be applied directly to cells, for example in a cell culture. If administered to a cell culture, the compound is preferably first suspended or dissolved in a suitable

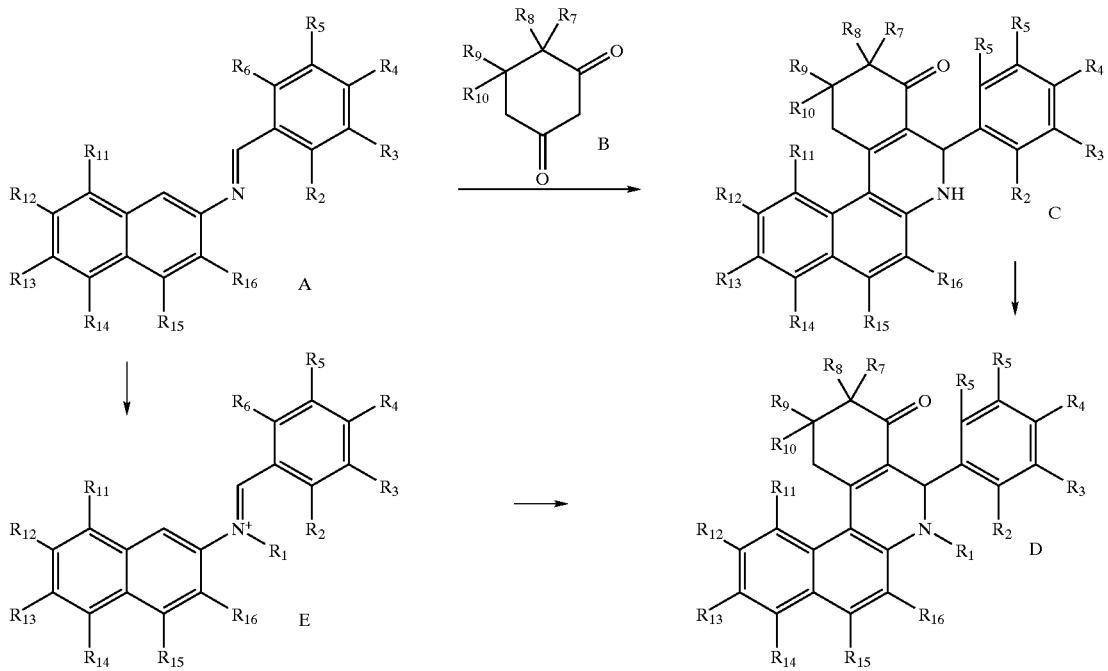

carrier. Suitable carriers include, without limitation, water, saline solution, dimethylsulfoxide (DMSO) and solutions thereof, cell culture media, and the like.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

A compound of formula 1 or a pharmaceutical composition containing same is administered via any of the usual and acceptable methods known in the art, either singly or in combination with another compound or compounds of the present invention or other pharmaceutical agents. These compounds or compositions can thus be administered orally, systemically (e.g., transdermally, intranasally or by suppository) or parenterally (e.g., intramuscularly, subcutaneously and intravenously), and can be administered either in the form of solid or liquid dosages including tablets, solutions, suspensions, aerosols, and the like, as discussed in more detail above. One can administer compounds of the invention by direct injection into a tumor. The formulation can be administered in a single unit dosage form for continuous treatment or in a single unit dosage form ad libitum when relief of symptoms is specifically required.

The effective dose of a compound of the invention will depend on the condition to be treated, the potency and absorption rate of the compound as formulated, the mode of administration, the age, weight, and health of the subject, and the like, and thus cannot be specified in advance. However, it is possible to estimate the dosage by methods known in the art. For example, one can obtain tumor cells from a patient by biopsy, and directly determine the concentration of a compound of the invention that is effective to inhibit the growth of cancerous tissue. From this measurement, one can calculate a dosage (depending on the route of administration) suitable for the patient.

EXAMPLES

The following examples are provided as a guide for the practitioner of ordinary skill in the art. Nothing in the examples is intended to limit the claimed invention. Unless otherwise specified, all reagents are used in accordance with the manufacturer's recommendations, and all reactions are performed at ambient temperature and pressure.

Example 1

Compound Preparation (A) The compound 1,3,6H-2,2-dimethyl-5-(3-bromo-4-dimethylamino)phenyl-benzo-[a]phenanthridin-4-one is synthesized by suspending 2-(3-bromo-4-dimethylaminobenzylidenylimino)-naphthalene in dimethylsulfoxide (DMSO), adding 5,5-dimethylcyclohexa-1,3-dione, and heating at about 50° C. until the reaction is judged complete by thin layer chromatography (tlc). The product is extracted with ether and recrystallized to provide 1,3,6H-2,2-dimethyl-5-(3-bromo-4-dimethylamino)phenyl-benzo[a]phenanthridin-4-one. Compounds of the invention are characterized by proton- and carbon nuclear magnetic resonance spectroscopy, mass spectroscopy, and elemental analyses.

(B) Proceeding as set forth in part (A) above, but substituting the following reactants for 2-(3-bromo-4-dimethylaminobenzylidenylimino)-naphthalene:

2-(2-bromobenzylidenylimino)-naphthalene, 2-(3-bromobenzylidenylimino)-naphthalene, 2-(4-bromobenzylidenylimino)-naphthalene, 2-(3,4-methylenedioxybenzylidenylimino)-naphthalene, 2-(3,4-dihydroxybenzylidenylimino)-naphthalene, and 2-(3,4-dimethoxybenzylidenylimino)-naphthalene, the following compounds are prepared:

1,3,6H-2,2-dimethyl-5-(2-bromo)phenyl-benzo[a]phenanthridin-4-one, 1,3,6H-2,2-dimethyl-5-(3-bromo)phenyl-benzo[a]phenanthridin-4-one, 1,3,6H-2,2-dimethyl-5-(4-bromo)phenyl-benzo[a]phenanthridin-4-one, 1,3,6H-2,2-dimethyl-5-(3,4-methylenedioxy)phenyl-benzo[a]phenanthridin-4-one, 1,3,6H-2,2-dimethyl-5-(3,4-dihydroxy)phenyl-benzo[a]phenanthridin-4-one, and 1,3,6H-2,2-dimethyl-5-(3,4-dimethoxy)phenyl-benzo[a]phenanthridin-4-one.

(C) Similarly, proceeding as in parts (A) and (B) above, but substituting cyclohexa-1,3-dione and 5-(4-butoxyphenyl)-cyclohexa-1,3-dione for 5,5-dimethylcyclohexa-1,3-dione, the following compounds are prepared:

1,3,6H-5-(3-bromo-4-dimethylamino)phenyl-benzo[a]phenanthridin-4-one, 1,3,6H-5-(2-bromo)phenyl-benzo[a]phenanthridin-4-one, 1,3,6H-5-(3-bromo)phenyl-benzo[a]phenanthridin-4-one, 1,3,6H-5-(4-bromo)phenyl-benzo[a]phenanthridin-4-one, 1,3,6H-5-(3,4-methylenedioxy)phenyl-benzo[a]phenanthridin-4-one, 1,3,6H-5-(3,4-dihydroxy)phenyl-benzo[a]phenanthridin-4-one, 1,3,6H-5-(3,4-dimethoxy)phenyl-benzo[a]phenanthridin-4-one, 1,3,6H-2-(4-butoxyphenyl)-5-(3-bromo-4-dimethylamino)phenyl-benzo[a]phenanthridin-4-one, 1,3,6H-2-(4-butoxyphenyl)-5-(2-bromo)phenyl-benzo[a]phenanthridin-4-one, 1,3,6H-2-(4-butoxyphenyl)-5-(3-bromo)phenyl-benzo[a]phenanthridin-4-one, 1,3,6H-2-(4-butoxyphenyl)-5-(4-bromo)phenyl-benzo[a]phenanthridin-4-one, 1,3,6H-2-(4-butoxyphenyl)-5-(3,4-methylenedioxy)phenyl-benzo[a]phenanthridin-4-one, 1,3,6H-2-(4-butoxyphenyl)-5-(3,4-dihydroxy)phenyl-benzo[a]phenanthridin-4-one, and 1,3,6H-2-(4-butoxyphenyl)-5-(3,4-dimethoxy)phenyl-benzo[a]phenanthridin-4-one, (D) Similarly, proceeding as set forth in parts (A), (B), and (C) above, but further reacting the product with dimethyl sulfate, diethyl sulfate, or butyl trifluoromethanesulfonate in dimethylformamide (DMF) under basic conditions at about 50° C., the following compounds are prepared:

1-methyl-3,6H-2,2-dimethyl-5-(3-bromo-4-dimethylamino)phenyl-benzo[a]phenanthridin-4-one, 1-methyl-3,6H-2,2-dimethyl-5-(2-bromo)phenyl-benzo[a]phenanthridin-4-one, 1-methyl-3,6H-2,2-dimethyl-5-(3-bromo)phenyl-benzo[a]phenanthridin-4-one, 1-methyl-3,6H-2,2-dimethyl-5-(4-bromo)phenyl-benzo[a]phenanthridin-4-one, 1-methyl-3,6H-2,2-dimethyl-5-(3,4-methylenedioxy)phenyl-benzo[a]phenanthridin-4-one, 1-methyl-3,6H-2,2-dimethyl-5-(3,4-dihydroxy)phenyl-benzo[a]phenanthridin-4-one, 1-methyl-3,6H-2,2-dimethyl-5-(3,4-dimethoxy)phenyl-benzo[a]phenanthridin-4-one, 1-methyl-3,6H-5-(3-bromo-4-dimethylamino)phenyl-benzo[a]phenanthridin-4-one, 1-methyl-3,6H-5-(2-bromo)phenyl-benzo[a]phenanthridin-4-one, 1-methyl-3,6H-5-(3-bromo)phenyl-benzo[a]phenanthridin-4-one, 1-methyl-3,6H-5-(4-bromo)phenyl-benzo[a]phenanthridin-4-one, 1-methyl-3,6H-5-(3,4-methylenedioxy)phenyl-benzo[a]phenanthridin-4-one, 1-methyl-3,6H-5-(3,4-dihydroxy)phenyl-benzo[a]phenanthridin-4-one, 1-methyl-3,6H-5-(3,4-dimethoxy)phenyl-benzo[a]phenanthridin-4-one, 1-methyl-3,6H-2-(4-butoxyphenyl)-5-(3-bromo-4-dimethylamino)phenyl-benzo[a]phenanthridin-4-one, 1-methyl-3,6H-2-(4-butoxyphenyl)-5-(2-bromo)phenyl-benzo[a]phenanthridin-4-one, 1-methyl-3,6H-2-(4-butoxyphenyl)-5-(3-bromo)phenyl-benzo[a]phenanthridin-4-one, 1-methyl-3,6H-2-(4-butoxyphenyl)-5-(4-bromo)phenyl-benzo[a]phenanthridin-4-one, 1-methyl-3,6H-2-(4-butoxyphenyl)-5-(3,4-methylenedioxy)phenyl-benzo[a]phenanthridin-4-one, 1-methyl-3,6H-2-(4-butoxyphenyl)-5-(3,4-dihydroxy)phenyl-benzo[a]phenanthridin-4-one, 1-methyl-3,6H-2-(4-butoxyphenyl)-5-(3,4-dimethoxy)phenyl-benzo[a]phenanthridin-4-one, 1-ethyl-3,6H-2,2-dimethyl-5-(3-bromo-4-dimethylamino)phenyl-benzo[a]phenanthridin-4-one, 1-ethyl-3,6H-2,2-dimethyl-5-(2-bromo)phenyl-benzo[a]phenanthridin-4-one, 1-ethyl-3,6H-2,2-dimethyl-5-(3-bromo)phenyl-benzo[a]phenanthridin-4-one, 1-ethyl-3,6H-2,2-dimethyl-5-(4-bromo)phenyl-benzo[a]phenanthridin-4-one, 1-ethyl-3,6H-2,2-dimethyl-5-(3,4-methylenedioxy)phenyl-benzo[a]phenanthridin-4-one, 1-ethyl-3,6H-2,2-dimethyl-5-(3,4-dihydroxy)phenyl-benzo[a]phenanthridin-4-one, 1-ethyl-3,6H-2,2-dimethyl-5-(3,4-dimethoxy)phenyl-benzo[a]phenanthridin-4-one, 1-ethyl-3,6H-5-(3-bromo-4-dimethylamino)phenyl-benzo[a]phenanthridin-4-one, 1-ethyl-3,6H-5-(2-bromo)phenyl-benzo[a]phenanthridin-4-one, 1-ethyl-3,6H-5-(3-bromo)phenyl-benzo[a]phenanthridin-4-one, 1-ethyl-3,6H-5-(4-bromo)phenyl-benzo[a]phenanthridin-4-one, 1-ethyl-3,6H-5-(3,4-methylenedioxy)phenyl-benzo[a]phenanthridin-4-one, 1-ethyl-3,6H-5-(3,4-dihydroxy)phenyl-benzo[a]phenanthridin-4-one, 1-ethyl-3,6H-5-(3,4-dimethoxy)phenyl-benzo[a]phenanthridin-4-one, 1-ethyl-3,6H-2-(4-butoxyphenyl)-5-(3-bromo-4-dimethylamino)phenyl-benzo[a]phenanthridin-4-one, 1-ethyl-3,6H-2-(4-butoxyphenyl)-5-(2-bromo)phenyl-benzo[a]phenanthridin-4-one, 1-ethyl-3,6H-2-(4-butoxyphenyl)-5-(3-bromo)phenyl-benzo[a]phenanthridin-4-one, 1-ethyl-3,6H-2-(4-butoxyphenyl)-5-(4-bromo)phenyl-benzo[a]phenanthridin-4-one, 1-ethyl-3,6H-2-(4-butoxyphenyl)-5-(3,4-methylenedioxy)phenyl-benzo[a]phenanthridin-4-one, 1-ethyl-3,6H-2-(4-butoxyphenyl)-5-(3,4-dihydroxy)phenyl-benzo[a]phenanthridin-4-one, 1-ethyl-3,6H-2-(4-butoxyphenyl)-5-(3,4-dimethoxy)phenyl-benzo[a]phenanthridin-4-one, 1-butyl-3,6H-2,2-dimethyl-5-(3-bromo-4-dimethylamino)phenyl-benzo[a]phenanthridin-4-one, 1-butyl-3,6H-2,2-dimethyl-5-(2-bromo)phenyl-benzo[a]phenanthridin-4-one, 1-butyl-3,6H-2,2-dimethyl-5-(3-bromo)phenyl-benzo[a]phenanthridin-4-one, 1-butyl-3,6H-2,2-dimethyl-5-(4-bromo)phenyl-benzo[a]phenanthridin-4-one, 1-butyl-3,6H-2,2-dimethyl-5-(3,4-methylenedioxy)phenyl-benzo[a]phenanthridin-4-one, 1-butyl-3,6H-2,2-dimethyl-5-(3,4-dihydroxy)phenyl-benzo[a]phenanthridin-4-one, 1-butyl-3,6H-2,2-dimethyl-5-(3,4-dimethoxy)phenyl-benzo[a]phenanthridin-4-one, 1-butyl-3,6H-5-(3-bromo-4-dimethylamino)phenyl-benzo[a]phenanthridin-4-one, 1-butyl-3,6H-5-(2-bromo)phenyl-benzo[a]phenanthridin-4-one, 1-butyl-3,6H-5-(3-bromo)phenyl-benzo[a]phenanthridin-4-one, 1-butyl-3,6H-5-(4-bromo)phenyl-benzo[a]phenanthridin-4-one, 1-butyl-3,6H-5-(3,4-methylenedioxy)phenyl-benzo[a]phenanthridin-4-one, 1-butyl-3,6H-5-(3,4-dihydroxy)phenyl-benzo[a]phenanthridin-4-one, 1-butyl-3,6H-5-(3,4-dimethoxy)phenyl-benzo[a]phenanthridin-4-one, 1-butyl-3,6H-2-(4-butoxyphenyl)-5-(3-bromo-4-dimethylamino)phenyl-benzo[a]phenanthridin-4-one, 1-butyl-3,6H-2-(4-butoxyphenyl)-5-(2-bromo)phenyl-benzo[a]phenanthridin-4-one, 1-butyl-3,6H-2-(4-butoxyphenyl)-5-(3-bromo)phenyl-benzo[a]phenanthridin-4-one, 1-butyl-3,6H-2-(4-butoxyphenyl)-5-(4-bromo)phenyl-benzo[a]phenanthridin-4-one, 1-butyl-3,6H-2-(4-butoxyphenyl)-5-(3,4-methylenedioxy)phenyl-benzo[a]phenanthridin-4-one, 1-butyl-3,6H-2-(4-butoxyphenyl)-5-(3,4-dihydroxy)phenyl-benzo[a]phenanthridin-4-one, 1-butyl-3,6H-2-(4-butoxyphenyl)-5-(3,4-dimethoxy)phenyl-benzo[a]phenanthridin-4-one.

Example 2

Formulations

The following example illustrates the preparation of representative pharmaceutical formulations containing an active compound of formula 1:

| (A) I.V. Formulation: | |
|---|---|
| Active compound | 0.01 g |
| Propylene glycol | 20.0 g |
| Polyethylene glycol 400 | 20.0 g |
| Tween ® 80 | 1.0 g |
| 0.9% Saline solution qs | 100.0 ml |

The active compound is dissolved in propylene glycol, polyethylene glycol 400 and Tween® 80. A sufficient quantity of 0.9% saline solution is then added with stirring to provide 100 mL of the I.V. solution which is filtered through a 0.2 µm membrane filter and packaged under sterile conditions.

| (B) Tablet Formulation: | |
|---|---|
| | parts by weight |
| Active compound | 25.0 |
| Magnesium stearate | 0.2 |
| Pregelatinized starch | 74.8 |

The above ingredients are dry-blended and loaded into #0 capsules containing about 100 mg active compound per capsule.

Example 3

Assay Construction (A) cDNAs corresponding to the complete open reading frame of RhoC were PCR amplified from pooled total cDNAs initially synthesized from placental, fetal brain, and fetal liver poly(A)$^+$ mRNAs (Clontech Laboratories, Inc.). First and second strand cDNA synthesis was performed using Superscript II reverse transcriptase (Life Technologies, Inc.) as previously described (E. L. Perkins et al., *Proc Natl Acad Sci USA* (1999) 96(5):2204–09). The 5' and 3' oligonucleotides for amplification were, respectively, RhoC 5' (5' CAAAAAATTGTTAATATACCTCTATACTT TAACGTCAAGGGGATCCatggctgcaatccgaaagaag 3') and RhoC 3' (5' CAGTTGAAGTGAACTTGCGGGGTTTTTC AGTATCTACGATTCATCTGCAGtcagagaatgggacagccc ct3'). PCR amplification was carried out using Bio-X-ACT (Bioline USA Inc., Kenilworth, N.J.) thermostable DNA polymerase according to the manufacturer instructions. Oligonucleotides were designed to amplify their target cDNAs and carry approximately 45 base pairs of homology at their 5' ends with the yeast expression vector pARC25B (GenBank AF359244) or its close relative pARC35B. The pARC35B vector contains the yeast GAL1 promoter, GAL4 transcription terminator, ARS sequence for replication, CEN sequence for mitotic transmission, and the LEU2 gene for selection in yeast.

After PCR, approximately 200 ng of amplified cDNA was cotransformed with approximately 100 ng of vector into yeast and transformants were selected for leucine prototrophy. Homologous recombination of the target cDNAs into pARC35B was confirmed by yeast whole cell PCR. Plasmids from at least three independent transformants were subsequently rescued into the *E. coli* strain DH5alpha via electroporation, and further characterized by restriction enzyme analysis and DNA sequencing of the RhoC open reading frame. The insert sequence was confirmed as identical to that of GenBank BC009177 (and many other RhoC clones).

Purified and sequenced RhoC expression plasmid was then linearized with SfiI which simultaneously removes the CEN/ARS sequence, and exposes 45 nucleotide segments that match to the 5' and 3' regions of the LYS2 gene, so that integration at the LYS2 locus can be detected. The linear plasmid was transformed into the yeast strain EIS20-2B and selected for leucine prototrophy. These colonies were then replica-plated to alpha amino-adipate plates to screen for those which had become lysine auxotrophs, indicating the replacement of the LYS2 gene with the expression vector. Several individual alpha-amino adipate-resistant transformants were clonally purified by streaking to rich media, and proper integration at the LYS2 locus was confirmed by whole cell PCR.

(B) Several correctly integrated isolates and controls were grown to saturation in synthetic media with 2% glucose (repressed) in a microtiter dish overnight at 30° C. The cultures were then diluted 1:400 into synthetic media with 2% galactose to induce expression of the RhoC protein. Measurements of culture density by absorbance at 600 nm were taken at intervals for approximately 48 hours. Growth inhibition was calculated relative to cells harboring integrated empty vector. RhoC-expressing cells typically grow to an optical density of about 20% that of vector alone after about 42 hours. This is scored as 80% growth inhibition.

A yeast strain expressing RhoC as described above was then screened against a library of over 110,000 low molecular weight organic compounds which represents a diverse collection derived from multiple commercial sources. All screening was done with initial compound concentrations of 5 µg/ml. Cells were grown overnight in synthetic media with 2% glucose (repressed) to late logarithmic/early stationary phase. The next day cells were washed once with synthetic media without a carbon source and diluted to a final $OD_{600}$ of 0.02 in synthetic media containing 2% galactose (induced). The diluted cells (90 µl) were added immediately to 96-well plates containing the test compound. The final volume in each well was 100 µl, and contained DMSO at a final concentration of 1%. As a control, cells containing vector (EIS20-2B with integrated vector plasmid) were similarly grown, washed and diluted to the same OD and then inoculated.

The plates were incubated at 30° C. for 40–42 hrs, and the $OD_{600}$ was read with a micro-titer plate reader (Molecular Device, Menlo Park, Calif.) after shaking. The effect of compounds was measured as percent of growth restoration using the following equation: Percent Growth Restoration= (TEST−MEDarc)/(MEDvec−MEDarc)×100, where TEST is the $OD_{600}$ of the well with test compound, MEDarc is the median value of $OD_{600}$ of the cells without compound, and MEDvec is the median value of $OD_{600}$ of vector-containing cells. Compounds showing □20% growth restoration were scored as hits. Compounds were later obtained in powder form and retested in dilutions from 0.5 µM to 128 µM.

(C) The compounds listed in the Table below showed excellent potency. The therapeutic index is derived by dividing the $EC_{50}$s by the $CC_{50}$ values.

| Structure | Compound | EC$_{50}$ | CC$_{50}$ | Index |
|---|---|---|---|---|
| | 1,3,6H-2,2-dimethyl-5-(3-bromo-4-dimethylamino)phenyl-benzo[a]-phenanthridin-4-one | | | |
| | 1,3,6H-2,2-dimethyl-5-(2-bromophenyl)-benzo[a]phenanthridin-4-one | | | |
| | 1,3,6H-2,2-dimethyl-5-(4-bromophenyl)-benzo[a]phenanthridin-4-one | | | |
| | 1,2-dihydro-3,6H-5-(3,4-methylenedioxyphenyl)-benzo[a]-phenanthridin-4-one | | | |
| | 1,2-dihydro-3,6H-5-(3-bromophenyl)-benzo[a]phenanthridin-4-one | | | |
| | 1,2-dihydro-3,6H-5-(3,4-dimethoxyphenyl)-benzo[a]phenanthridin-4-one | | | |

| Structure | Compound | EC₅₀ | CC₅₀ | Index |
|---|---|---|---|---|
| 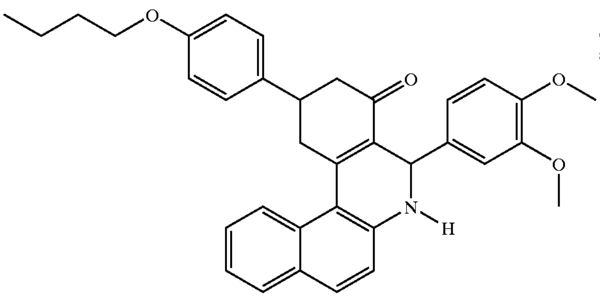 | 1,3,6H-2-(4-butoxyphenyl)-5-(3,4-dimethoxyphenyl)-benzo[a]phenanthridin-4-one | | | |

(D) Chemotaxis: Chemotaxis was carried out using ChemoTX plates obtained from Neuroprobe Inc. (Gaithersburg, Md.). A monocyte cell line, THP-1, was obtained from ATCC. The cells were pretreated with 30 µM compound in RPMI medium containing 10% fetal bovine serum for 2 hours, washed twice with the same medium without serum, and resuspended in the serum-free medium containing 30 µM compound. The monocyte chemoattractant protein-1 (MCP-1) was diluted in the serum free RPMI medium to 0.25 nM and aliquoted into the wells of the ChemoTX plate. The framed membrane filter (8 µm pore size) was assembled and the cells (100,000 cells in 60 µl) were loaded on top of the filter areas. The ChemoTX plate was incubated at 37° C. for 2 hours. After removing the framed filter, the plate was centrifuged and the cells in each well were labeled with 5 µM Calcein AM (Molecular Probes) for 1 hour at 37° C. The cells were washed once with PBS and fluorescence was measured at excitation wavelength of 485 nm and emission of 538 nm. The results are the mean absorbance readings from quadruplicate wells for each parameter.

What is claimed is:

1. A compound of formula 1:

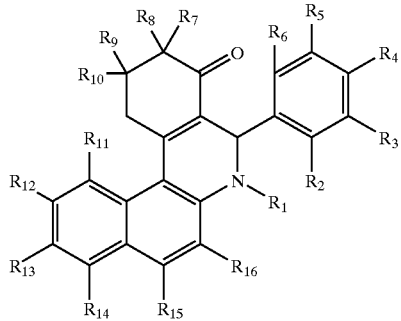

wherein $R_1$ is H, OH, or lower alkyl;

$R_2$, $R_3$, $R_4$, and $R_6$ are each independently H, halo, lower alkyl, OH, lower alkoxy, $NH_2$, lower alkylamino, di(lower alkyl)amino, SH, lower alkylthio, $NO_2$, or two residues together form a heterocyclic ring;

$R_5$ is H, lower alkyl, lower alkoxy, $NH_2$, lower alkylamino, di(lower alkyl)amino, SH, lower alkylthio, $NO_2$, or two residues together form a heterocyclic ring;

$R_7$, and $R_8$ are each independently H, lower alkyl, OH, $NH_2$, aryl, or aralkyl, where aryl and aralkyl are substituted with 0–3 moieties selected from the group consisting of halo, OH, $NH_2$, lower alkyl, lower alkoxy, SH, lower alkylthio, and lower alkylamino;

$R_9$, and $R_{10}$ are each independently H, lower alkyl, OH, $NH_2$, aryl, or aralkyl, where aryl and aralkyl are substituted with 0–3 moieties selected from the group consisting of halo, OH, $NH_2$, lower alkyl, SH, lower alkylthio, and lower alkylamino;

$R_{11}$, $R_{12}$, $R_{13}$, $R_{14}$, $R_{15}$, and $R_{16}$ are each independently H, halo, lower alkyl, OH, lower alkoxy, or $NO_2$;

and pharmaceutically acceptable salts thereof.

2. The compound of claim 1, wherein $R_{11}$, $R_{12}$, $R_{13}$, $R_{14}$, $R_{15}$, and $R_{16}$ are each H.

3. The compound of claim 2, wherein $R_1$ is H.

4. The compound of claim 3, wherein $R_7$, $R_8$, $R_9$, and $R_{10}$ are each H.

5. The compound of claim 4, wherein $R_3$ is Br.

6. The compound of claim 4, wherein $R_3$ and $R_4$ are each methoxy.

7. The compound of claim 4, wherein $R_3$ and $R_4$ together form methylenedioxy.

8. The compound of claim 3, wherein $R_7$ and $R_8$ are each H, and $R_9$ and $R_{10}$ are each methyl.

9. The compound of claim 8, wherein $R_2$ is Br.

10. The compound of claim 8, wherein $R_4$ is Br.

11. The compound of claim 8, wherein $R_3$ is Br and $R_4$ is dimethylamino.

12. The compound of claim 3, wherein $R_7$, $R_8$ and $R_{10}$ are each H and $R_9$ is aryl, or aralkyl, where aryl and aralkyl are substituted with 0–3 moieties selected from the group consisting of halo, OH, $NH_2$, lower alkyl, SH, lower alkylthio, and lower alkylamino.

13. The compound of claim 12, wherein $R_3$ and $R_4$ are each methoxy.

14. A pharmaceutical composition comprising:

an effective amount of a compound of formula 1

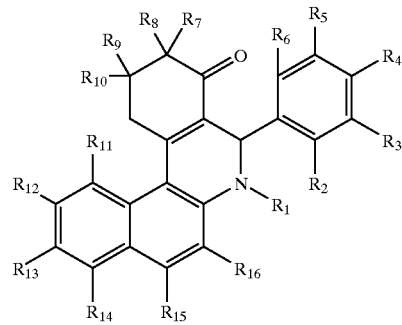

wherein $R_1$ is H, OH, or lower alkyl;

$R_2$, $R_3$, $R_4$, and $R_6$ are each independently H, halo, lower alkyl, OH, lower alkoxy, $NH_2$, lower alkylamino, di(lower alkyl)amino, SH, lower alkylthio, $NO_2$, or two residues together form a heterocyclic ring;

$R_5$ is H, lower alkyl, lower alkoxy, $NH_2$, lower alkylamino, di(lower alkyl)amino, SH, lower alkylthio, $NO_2$, or two residues together form a heterocyclic ring;

$R_7$, and $R_8$ are each independently H, lower alkyl, OH, $NH_2$, aryl, or aralkyl, where aryl and aralkyl are substituted with 0–3 moieties selected from the group consisting of halo, OH, $NH_2$, lower alkyl, lower alkoxy, SH, lower alkylthio, and lower alkylamino;

$R_9$, and $R_{10}$ are each independently H, lower alkyl, OH, $NH_2$, aryl, or aralkyl, where aryl and aralkyl are substituted with 0–3 moieties selected from the group consisting of halo, OH, $NH_2$, lower alkyl, SH, lower alkylthio, and lower alkylamino;

$R_{11}$, $R_{12}$, $R_{13}$, $R_{14}$, $R_{15}$, and $R_{16}$ are each independently H, halo, lower alkyl, OH, lower alkoxy, or $NO_2$;

or a pharmaceutically acceptable salt thereof;

and a pharmaceutically acceptable excipient.

* * * * *